United States Patent [19]

Tucker

[11] 4,275,058

[45] Jun. 23, 1981

[54] β-ADRENERGIC BLOCKING ALKANOLAMINE DERIVATIVES

[75] Inventor: Howard Tucker, Macclesfield, England

[73] Assignee: Imperial Chemical Industries Limited, London, England

[21] Appl. No.: 9,362

[22] Filed: Feb. 5, 1979

[30] Foreign Application Priority Data

Feb. 8, 1978 [GB] United Kingdom ............... 5042/78

[51] Int. Cl.³ .................... N61K 31/135; C07C 87/28
[52] U.S. Cl. .............................. 424/199; 260/501.17; 424/211; 424/230; 424/317; 424/330; 564/349; 564/351
[58] Field of Search ............... 260/570.7 OH, 501.17; 424/330, 199, 211, 230, 317; 564/399, 351

[56] References Cited

U.S. PATENT DOCUMENTS

| 3,337,628 | 8/1967 | Crowther et al. ............... 260/570.7 |
| 3,415,873 | 12/1968 | Stevens ........................ 260/570.7 X |
| 3,501,769 | 3/1970 | Crowther et al. .............. 260/501.17 |
| 3,534,085 | 10/1970 | Narayanan et al. ... 260/570.7 OH X |
| 3,646,066 | 2/1972 | Narayanan et al. ... 260/570.7 OH X |
| 4,029,676 | 6/1977 | Hauck et al. .......... 260/570.7 OH X |
| 4,048,231 | 9/1977 | Hauck et al. ............. 260/570.7 OH |
| 4,127,675 | 11/1978 | Murakami et al. .... 260/570.7 OH X |

FOREIGN PATENT DOCUMENTS 52-106946  8/1975  Japan ..................................... 260/570.7

OTHER PUBLICATIONS

British J. Pharm., 1970, 39, 139, Levy et al.
British J. Pharm., 1973, 49, 514, Levy.
Fitzgerald et al., Federation Proceedings, 1975, 721.
Manufacturing Chemist, 37, p. 56 (1966).

Primary Examiner—Thomas A. Waltz
Attorney, Agent, or Firm—Cushman, Darby & Cushman

[57] ABSTRACT

1-Indanyloxy- or tetrahydronaphthyloxy-3-amino-2-butanol derivatives, especially erythro-1-(7-methylindan-4-yloxy)-3-isopropylaminobutan-2-ol, processes for their manufacture and pharmaceutical compositions containing them. The compounds possess peripherally-selective β-adrenergic blocking activity.

6 Claims, No Drawings

β-ADRENERGIC BLOCKING ALKANOLAMINE DERIVATIVES

This invention relates to new alkanolamine derivatives which possess peripherally-selective β-adrenergic blocking activity.

It is known that many 1-aryloxy-3-amino-2-propanol derivatives possess β-adrenergic blocking properties, and it is also known that differential blockade of the β-adrenergic receptors in the heart and in the peripheral vasculature is possible. Compounds are known for which a dose of administration may be selected which will cause blockade of the cardiac (or $\beta_1$) receptors but which will not cause blockade of the peripheral (or $\beta_2$) receptors. These are known as cardioselective β-adrenergic blocking agents and examples of such compounds are practolol and atenolol. Compounds are also known which are more effective in blocking the β-adrenergic receptor of the peripheral vasculature than those of the heart. Such compounds are known, by analogy with cardioselective agents, as vascular-selective β-adrenergic blocking agents. No compound is known, however, which produces clinically effective peripheral blockade but does not at the same time produce cardiac blockade. For example, propanolol is slightly more effective in blocking peripheral receptors than in blocking cardiac receptors, but is so active that it produces cardiac blockade at the lowest doses used.

It is further known that insertion of a methyl group into the propanol side-chain, to produce 1-aryloxy-3-amino-2-butanol derivatives, in some cases enhances the vascular selectivity of the compounds, but in general reduces the overall β-adrenergic blocking activity. This has been demonstrated particularly in the case of α-methylpropranolol where there is a clear reduction in potency and an arguable increase in vascular-selectivity (Todd, Pharmacologist, 1976, 18, 138).

We have now found, and herein lies our invention, that α-methyl analogues of certain 1-indanyloxy- or 1-tetrahydronaphthyloxy-3-amino-2-propanol derivatives possess a high level of peripheral β-adrenergic blocking activity but at doses which produce such activity have no cardiac β-adrenergic blocking activity.

According to the invention there is provided an alkanolamine derivative of the formula:

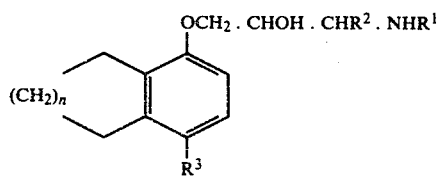

wherein
$R^1$ is alkyl of up to 6 carbon atoms which is branched at the α-carbon atom, wherein $R^2$ is alkyl of up to 3 carbon atoms, wherein $R^3$ is hydrogen, halogen or alkyl of up to 3 carbon atoms and wherein n is 1 to 2, or an acid-addition salt thereof.

$R^1$ may be, for example, isopropyl or t-butyl, and is preferably isopropyl.

$R^2$ may be, for example, methyl or ethyl, and is preferably methyl.

$R^3$ may be for example, hydrogen, chlorine, bromine, methyl or ethyl, and is preferably methyl.

n is preferably 1.

It will be observed that the alkanolamine derivative of the invention possesses two asymmetric carbon atoms, namely those of the —CHOH— group and the —CHR$^2$— group, and that it can therefore exist in two racemic diastereoisomeric forms, the threo and erythro forms, and four optically-active forms. these being the (+) and (—) isomers of each of the racemic forms. It is to be understood that this invention encompasses any one of these isomeric forms which possess peripherally-selective β-adrenergic blocking activity as defined below, it being a matter of common general knowledge how any particular isomer may be isolated and how any peripherally-selective β-adrenergic blocking activity it may possess may be measured.

It is to be understood that in general an optical isomer which has the (S)-absolute configuration of the —CHOH— group is more active as a β-adrenergic blocking agent than the corresponding isomer which has the (R)-absolute configuration. We have also found that in general the erythro-isomer is more peripherally-selective than the corresponding threo-isomer, but that both threo- and erythro-isomers of the compounds of the present invention possess the required selectivity.

A suitable acid-addition salt of an alkanolamine derivative of the invention is, for example, a salt derived from an inorganic acid, for example a hydrochloride, hydrobromide, phosphate or sulphate, or a salt derived from an organic acid, for example an oxalate, lactate, tartrate, acetate, salicylate, citrate, benzoate, β-naphthoate, adipate or 1,1-methylene-bis(2-hydroxy-3-naphthoate), or a salt derived from an acidic synthetic resin, for example a sulphonated polystyrene resin.

Specific alkanolamine derivatives of the invention are hereinafter described in the Examples. Of these, particularly preferred compounds are erythro-1-(7-methylindan-4-yloxy)-3-isopropylaminobutan-2-ol; threo-1-(7-methylindan-4-yloxy)-3-isopropylaminobutan-2-ol and erythro-(indan-4-yloxy)-3-isopropylaminobutan-2-ol and the acid-addition salts thereof.

The alkanolamine derivative of the invention may be manufactured by any process known to be useful for the manufacture of chemically-analogous compounds.

A preferred process for the manufacture of an alkanolamine derivative of the invention comprises the reaction of a compound of the formula:

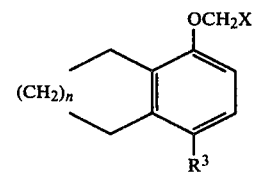

wherein $R^3$ and n have the meanings stated above and wherein X stands for the group:

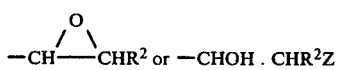

wherein $R^2$ has the meaning stated above and wherein Z stands for a displaceable radical, with an amine of the formual $R^1NH_2$. wherein $R^1$ has the meaning stated above.

Z may be, for example, a halogen atom, for example a chlorine or bromine atom, or it may be a sulphonyloxy radical, for example the methane-sulphonyloxy or p- toluenesulphonyloxy radical. The reaction may be carried out in a diluent or solvent, for example water, an alcohol, for example methanol or ethanol, or an excess of an amine of the formula $R^1NH_2$, wherein $R^1$ has the meaning stated above, and it may be carried out at a temperature up to the boiling point of the diluent or solvent.

The starting material may be obtained by the reaction of a compound of the formula:

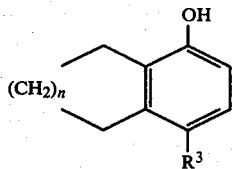

wherein $R^3$ and n have the meanings stated above, with an epoxide of the formula:

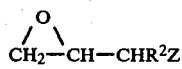

wherein $R^2$ and Z have the meanings stated above. It may alternatively be obtained by the reaction of a compound of the formula:

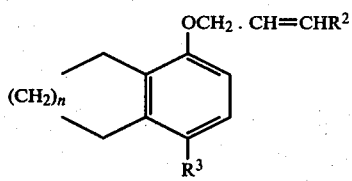

wherein $R^2$, $R^3$ and n have the meanings stated above, with a peroxide, for example hydrogen peroxide.

A compound which has the threo-configuration of the —CHOH— and —$CHR^2$— groups may be converted into the corresponding compound which has the erythro-configuration of said groups by successive protection of the secondary amino function —$NHR^1$— by acetylation with acetyl chloride, replacement of the hydroxy function by chlorine by reaction with thionyl chloride (this replacement causing no inversion of the stereo-chemistry at the carbon atom of the original —CHOH— group), and then replacement of the chlorine by hydroxy by reaction with an alkali metal hydroxide (this replacement causing inversion of the sterochemistry at the said carbom atom), the alkali metal hydroxide simultaneously removing the amino-acetyl protecting group by hydrolysis.

Optically-active enantiomorphs of the alkanolamine derivative of the invention may be obtained by the resolution by conventional means of the corresponding racemic alkanolamine derivative of the invention.

The said resolution may be carried out by reacting the racemic alkanolamine derivative with an optically-active acid, followed by fractional crystallisation of the diastereoisomeric mixture of salts thus obtained from a diluent or solvent, for example ethanol, whereafter the optically-active alkanolamine derivative is liberated from the salt by treatment with a base. A suitable optically-active acid is, for example (+)- or (−)-0,0-di-p-toluoyltartaric acid or (−)-2,3:4,5-di-O-isopropylidene-2-keto-L-gulonic acid.

The resolution process may be facilitated by treating the partially resolved alkanolamine derivative in free base form obtained after a single fractional crystallisation of the diastereoisomeric mixture of salts with a solubilishing agent, for example a primary amine, for example allylamine, in a relatively non-polar diluent or solvent, for example petroleum ether.

The alkanolamine derivative of the invention in free base form may be converted into an acid-addition salt thereof by reaction with an acid by conventional means.

As stated above, an alkanolamine derivative of the invention possess peripherally-selective $\beta$-adrenergic blocking activity. This may be demonstrated by its ability to antagonise the effect of a catecholamine such as isoprenaline in lowering the blood pressure of a perfused denervated hind limb of a dog at a dose which does not antagonise the effect of the same catecholamine in increasing the heart rate of the dog. Because of this selective activity a dose may be selected for the administration of such an alkanolamine derivative to a warm-blooded mammal such that $\beta$-adrenergic blockade of the peripheral blood vessels may be produced without unwanted effects on the heart. At a dose of an alkanolamine derivative of the invention which produces effective peripheral $\beta$-adrenergic blockade in the dog, no symptom of toxicity is apparent.

The alkanolamine derivative of the invention may be administered to warm-blooded animals, including man, in the form of a pharmaceutical composition comprising as active ingredient at least one alkanolamine derivative of the invention, or an acid-addition salt thereof, in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the alkanolamine derivative of the invention, one or more drugs selected from sedatives, for example phenobarbitone, meprobamate, chloropromazine and the benzodiazepine sedative drugs, for example chlordiazepoxide and diazepam; analgesic agents, for example acetylsalicylic acid, codeine and paracetamol; hypotensive agents, for example reserpine, bethanidine and guanethidine; and agents used in the treatment of Parkinson's disease and other tremors, for example benzhexol.

When used for the treatment of tremor, migraine, anxiety, schizophrenia, glaucoma or hypertension in man, it is expected that the alkanolamine derivative would be given to man at a total oral dose of between 2 mg. and 100 mg. daily, at doses spaced at 6–8 hourly intervals, or at an intravenous dose of between 0.2 mg. and 5 mg.

Preferred oral dosage forms are tablets or capsules containing between 2 and 100 mg., and preferably 1 mg. or 10 mg. of active ingredient. Preferred intravenous dosage forms are sterile aqueous solutions of the alkanolamine derivative or of a non-toxic acid-addition salt thereof, containing between 0.05% and 1% w/v of active ingredient, and more particularly containing 0.1% w/v of active ingredient.

The invention is illustrated but not limited by the following Examples:

EXAMPLE 1

A mixture of trans-2,3-epoxy-1-(7-methylindan-4-yloxy)-butane (19.9 g.), isopropylamine (100 ml.) and water (100 ml.) is heated under reflux for 16 hours and then evaporated to dryness under reduced pressure. The residue is dissolved in a mixture of concentrated aqueous hydrochloric acid (50 ml.) and water (50 ml.), the solution becoming hot during the dissolution. The solution is cooled and filtered and the solid product is crystallised from a 4:1 v/v mixture of ethanol and methanol. There is thus obtained erythro-1(7-methylindan-4-yloxy)-3-isopropylaminobutan-2-ol hydrochloride m.p. 222°–224° C.

The trans-2,3-epoxy-1-(7-methylindan-4-yloxy)butane used as starting material may be obtained by either of the following processes:

A. A solution of 7-methylindan-4-ol (118 g.) in dry N,N-dimethylformamide (296 ml.) is added during 30 minutes to a stirred suspension of sodium hydride (20.8 g.) in dry N,N-dimethylformamide at such a rate that the temperature of the mixture does not exceed 30° C. The mixture is stirred at laboratory temperature for a further 30 minutes and trans-crotyl chloride (106 ml.) is then added during 30 minutes. The mixture is stirred at laboratory temperature for 16 hours and water (1200 ml.) is then added at such a rate that the temperature of the mixture does not exceed 30° C. The aqueous layer is decanted off and the residue is stirred with cyclohexane (340 ml.). The mixture is filtered and the filtrate is washed once with aqueous 2 N-sodium hydroxide solution (240 ml.) and six times with saturated aqueous sodium chloride solution (120 ml. each time), dried over magnesium sulphate and evaporated to dryness under reduced pressure. The residue is crystallised from ethanol (at −7° C.) and there is thus obtained 1-(7-methylindan-4-yloxy) but-trans-2-ene, m.p. 29°–29.5° C.

A mixture of the above compound (110 g.) acetonitrile (115 ml.), hydrogen peroxide(125 ml. of a 50% w/w aqueous solution), anhydrous potassium hydrogen carbonate (44 g.) and methanol (1300 ml.) is stirred at laboratory temperature for 5 days and is then poured into water (5.3 liters). The mixture is filtered and the solid product is washed with water (700 ml.), dried at laboratory temperature and crystallised from petroleum ether, b.p. 60°–80° C. (570 ml.). There is thus obtained trans-2,3-epoxy-1-(7-methylindan-4-yloxy)butane, m.p. 68°–69° C.

A solution of bromine (63.3 g.) in methylene chloride (50 ml.) is added dropwise to a cooled, stirred solution of cis-crotyl alcohol (28.5 g.) in methylene chloride (50 ml.) and the mixture is stirred for 30 minutes at laboratory temperature and is then washed successively with dilute aqueous sodium thiosulphate solution and then with water, dried over magnesium sulphate and evaporated to dryness under reduced pressure. The residue is distilled under reduced pressure and there is thus obtained threo-2,3-dibromobutan-1-ol, b.p. 108°–110° C./13 mm.Hg.

A solution of the above compound (140 g.) in diethyl ether (700 ml.) and a solution of potassium hydroxide (45 g.) in water (400 ml.) are vigorously stirred together for 6 hours and the two layers are then separated. The ethereal layer is washed repeatedly with saturated aqueous sodium chloride solution until the washings are no longer alkaline and is then dried over magnesium sulphate and evaporated to dryness. The residue is distilled under reduced pressure and there is thus obtained erythro-3-bromo-1,2-epoxybutane, b.p. 39°–42° C./20 mm.Hg.

A stirred mixture of the above compound (33 g.), 7-methylindan-4-ol (25.2 g.), sodium hydroxide (7.5 g.), water (250 ml.) and 1,2-dimethoxyethane (25 ml.) is heated at 60° C. for 15 hours, cooled and extracted 4 times with chloroform (75 ml. each time). The combined extracts are washed with water until the washings are no longer alkaline, dried over magnesium sulphate and evaporated to dryness under reduced pressure. The residue is stirred with petroleum ether (b.p. 40°–60° C.) until it solidifies, and the solid is crystallised from a 2:1 v/v mixture of cyclohexane and petroleum ether (b.p. 60°–80° C.). There is thus obtained trans-2,3-epoxy-1-(7-methylindan-4-yloxy)butane, m.p. 68°–69° C.

EXAMPLE 2

The process described in Example 1 is repeated except that cis-2,3-epoxy-1-(7-methylindan-4-yloxy)butane [prepared by a similar process to that described in the last paragraph of Example 1 from the known (J. Organic Chemistry, 1956, 21, 429) threo-3-bromo-1,2-epoxybutane] is used in place of the trans-isomer. There is thus obtained threo-1-(7-methylindan-4-yloxy)-3-isopropylaminobutan-2-ol hydrochloride, m.p. 164°–166° C.

EXAMPLE 3

The process described in Example 1 (first paragraph; starting material prepared by Method B) or 2 is repeated except that the appropriate 7-substituted-or unsubstituted-indan-4-ol, the appropriate 3-bromo-1,2-epoxybutane and the appropriate amine are used as starting materials. There are thus obtained the compounds described in the following table:

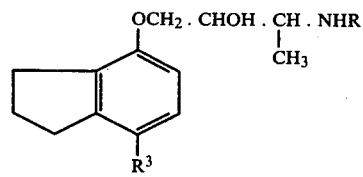

| $R^1$ | $R^3$ | isomer | m.p.(°C.) |
|---|---|---|---|
| isopropyl | H | erythro | free base 103–106 |
| isopropyl | H | threo | hydrochloride 179–181 |
| t-butyl | H | threo | hydrogen oxalate 162–163 |
| isopropyl | ethyl | threo | hydrochloride 175–177 |
| isopropyl | chloro | threo | hydrochloride 174.5–175.5 |

The 7-ethylindan-4-ol used as starting material may be obtained as follows:

3-Chloropropionyl chloride (133 g.) is added in portions of 5–10 ml. to molten 4-ethylphenol (63.8 g.) which is heated at 95°–100° C. When addition is complete the mixture is heated at 95°–100° C. for 90 minutes and is then kept at laboratory temperature for 18 hours. The mixture is shaken with ice-water (200 ml.) and diethyl ether (100 ml.) and the organic layer is separated. The aqueous layer is extracted with diethyl ether (50 ml.) and the combined organic solutions are washed twelve times with aqueous 2 N-sodium hydroxide solution (50 ml. each time) and then dried over magnesium sulphate and evaporated to dryness. The residue is distilled and there is thus obtained 4-ethylphenyl-3-chloropropionate, b.p. 121°–122° C./1.5 mm.Hg.

A mixture of the above compound (87.9 g.) and aluminium chloride (110 g.) is heated at 165°–170° C. for 5 hours, cooled and ice-water (200 ml.) is cautiously added. The mixture is steam-distilled and distillate is extracted three times with diethyl ether (50 ml. each time). The combined extracts are dried over magnesium sulphate and evaporated to dryness and the residue is crystallised from cyclohexane. There is thus obtained 4-ethyl-7-hydroxyindan-1-one, m.p. 89°–94° C.

A stirred mixture of the above compound (9.3 g.), amalgamated zinc (35 g.), water (35 ml.) and concentrated aqueous hydrochloric acid (35 ml.) is heated under reflux for 16 hours and the liquid phase is then decanted off the metallic residue and extracted with toluene (25 ml.). The toluene is evaporated off, the residue is dissolved in diethyl ether and the solution is dried over magnesium sulphate and evaporated to dryness. The residue is crystallised from petroleum ether (b.p. 60°–80° C.) and there is thus obtained 7-ethylindan-4-ol, m.p. 49°–51° C.

EXAMPLE 4

The process described in Example 2 is repeated exept that threo-2,3-epoxy-1-(5,6,7,8-tetrahydronaphth-1-yloxy)butane is used as starting material. There is thus obtained threo-1-(5,6,7,8-tetrahydronaphth-1-yloxy)-3-isopropylaminobutan-2-ol hydrochloride, m.p. 218°–224° C.

EXAMPLE 5

A mixture of trans-2,3-epoxy-1-(7-methylindan-4-yloxy)pentane (1.3 g.), isopropylamine 10 ml. and water (10 ml.) is heated under reflux for 16 hours, cooled and evaporated to dryness under reduced pressure. The residue is shaken with aqueous 2 N-hydrochloric acid (25 ml.) and ethyl acetate (25 ml.) and the organic layer is separated, dried over magnesium sulphate and evaporated to dryness. The residue is applied in ethyl acetate solution to thick-layer silica gel chromatography plates (20 cm.×20 cm.×2 mm. thick, Merck $F_{254}$) and the plates are developed with a 100:20:3 v/v mixture of ethyl acetate, ethanol and triethylamine. The relevant band is separated and extracted with methanol, the solution is filtered and the filtrate is evaporated to dryness. The residue is dissolved in chloroform, the solution is filtered and the filtrate is evaporated to dryness. The residue is crystallised from petroleum ether (b.p. 60°–80° C.) and there is thus obtained erythro-1-(7-methylindan-4-yloxy)-3-isopropylaminopentan-2-ol, m.p.72°–73° C.

The trans-2,3-epoxy-1-(7-methylindan-4-yloxy)pentane used as starting material may be obtained as follows:

A mixture of 7-methylindan-4-ol (1.48 g.), tetrahydrofuran (25 ml.) and sodium hydride (0.4 g. of a 60% dispersion in mineral oil) is stirred at laboratory temperature for 90 minutes, and a solution of erythro-3-bromo-1,2-epoxy-pentane (2.2 g.; prepared from cis-pent-2-ene-1-ol by a similar method to that described in part B of Example 1) in tetrahydrofuran (10 ml.) is then added during 10 minutes. The mixture is heated under reflux for 16 hours, N,N-dimethylformamide (10 ml.) is added and the mixture is heated under reflux for a further 84 hours and is then poured into an equal volume of water. The mixture is extracted twice with diethyl ether (25 ml. each time) and the combined extracts are washed with aqueous 2 N-sodium hydroxide solution (25 ml.) and twice with saturated aqueous sodium chloride solution (10 ml. each time), dried over magnesium sulphate and evaporated to dryness. The residue consists of trans-2,3-epoxy-1-(7-methylindan-4-yloxy)pentane which is used without further purification.

EXAMPLE 6

Acetyl chloride (1.03 ml.) is added to a stirred mixture of threo-1-(7-methylindan-4-yloxy)-3-isopropylamino-butan-2-ol (4.0 g.), methylene chloride (50 ml.) and triethylamine (1.5 ml.) and the mixture is stirred at laboratory temperature for 2 hours and is then washed successively with water (25 ml.), twice with aqueous 2 N-hydrochloric acid (25 ml. each time), and three times with water (25 ml. each time), is dried over magnesium sulphate and is evaporated to dryness under reduced pressure. Thionyl chloride (6 ml.) is added to the residue and after the exothermic reaction is over the mixture is kept at laboratory temperature for 30 minutes. The excess of thionyl chloride is distilled off under reduced pressure and the residue is stirred for 48 hours with a mixture of aqueous 7 N-sodium hydroxide solution, water (15 ml.) and N,N-dimethylformamide (15 ml.). More water (30 ml.) is added and the mixture is extracted three times with ethyl acetate (25 ml. each time). The combined extracts are dried over magnesium sulphate and evaporated to dryness, and the residue is crystallised from isopropanol. There is thus obtained erythro-1-(7-methylindan-4-yloxy)-3-isopropylaminobutan-2-ol, m.p. 90.5°–93.5° C.

EXAMPLE 7

A solution of (−)-di-p-toluoyl-(L)-tartaric acid (7.13 g.) in ethanol (15 ml.) is added to a solution of (±)-threo-1-(7-methylindan-4-yloxy)-3-isopropylaminobutan-2-ol (5.12 g.) in ethanol (15 ml.) and the mixture is boiled for 3 minutes and then allowed to cool. The mixture is filtered and the solid residue is crystallised twice from ethanol. The di-p-toluoyltartrate salt thus obtained (m.p. 114.5°–116° C.) is shaken with aqueous 2 N-sodium hydroxide solution (50 ml.) and ethyl acetate (50 ml.) and the organic layer is separated, washed with water, dried over magnesium sulphate and evaporated to dryness. The residue is dissolved in diethyl ether, an excess of saturated ethereal hydrogen chloride is added and the mixture is filtered. The residue is crystallised from isopropanol and there is thus obtained (+)-threo-1-(7-methylindan-4-yloxy)-3-isopropylaminobutan-2-ol hydrochloride, m.p. 173.5°–175° C.; $[\alpha]_{23}{}^{D}= +41.3°$ (methanol).

The combined ethanolic filtrates from the isolation and crystallisation of the di-p-toluoyltartrate salt described above are evaporated to dryness and the residue is shaken with aqueous 10 N-sodium hydroxide solution (25 ml.) and ethyl acetate (25 ml.). The organic layer is separated, washed with water, dried over magnesium sulphate and evaporated to dryness. The residue is dissolved in ethanol (10 ml.) and a solution of (+)-di-p-toluoy-(D)-tartaric acid (2.1 g.) in ethanol (10 ml.) is added. The mixture is boiled for 3 minutes and then allowed to cool. The precipitated salt is crystallised and the free base is isolated and converted to a hydrochloride salt by a similar procedure to that described in the preceding paragraph. There is thus obtained (−)-threo-1-(7-methylindan-4-yloxy)-3-isopropylaminobutan-2-ol hydrochloride, m.p. 173.5°–175° C.; $[\alpha]_{23}{}^{D}= -41.1°$ (methanol).

What we claim is:

1. The compond erythro-1-(7-methylindan-4-yloxy)-3-isopropylaminobutan-2-ol or an acid-addition salt thereof.

2. An acid-addition salt as claimed in claim 1 which is a hydrochloride, hydrobromide, phosphate, sulphate, oxalate, lactate, tartrate, acetate, salicylate, citrate, benzoate, β-naphthoate, adipate or 1,1-methylene-bis-(2-hydroxy-3-naphthoate).

3. A phrmaceutical composition comprising as active ingredient an effective amount to treat tremor, migraine, anxiety, schizophrenia, glaucoma, or hypertension in man of the compound of claim 1 or an acid-addition salt thereof in association with a pharmaceutically acceptable diluent or carrier therefor.

4. The composition of claim 3 in the form of a tablet, capsule, aqueous or oily solution or suspension, emulsion, injectable aqueous or oily solution or suspension, dispersible powder, spray or aerosol formulation.

5. The composition of claim 3 which also includes one or more drugs selected from sedatives, analgesic agents, hypotensive agents, and agents used in the treatment of Parkinson's disease and other tremors.

6. A method for the treatment of tremor, migraine, anxiety, schizophrenia, glaucoma or hypertension in man which comprises administering to man an effective amount of the compound of claim 1 or an acid-addition salt thereof.